US011229778B2

(12) United States Patent
Bodner

(10) Patent No.: US 11,229,778 B2
(45) Date of Patent: Jan. 25, 2022

(54) OPTIMIZED INTRATHECAL DRUG DELIVERY

(71) Applicant: Medtronic, Inc., Minneapolis, MN (US)

(72) Inventor: Jeffrey Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 309 days.

(21) Appl. No.: 16/444,209

(22) Filed: Jun. 18, 2019

(65) Prior Publication Data
US 2019/0388663 A1 Dec. 26, 2019

Related U.S. Application Data

(60) Provisional application No. 62/687,889, filed on Jun. 21, 2018.

(51) Int. Cl.
*A61M 31/00* (2006.01)

(52) U.S. Cl.
CPC ....... *A61M 31/002* (2013.01); *A61M 2205/04* (2013.01); *A61M 2205/3303* (2013.01); *A61M 2205/3523* (2013.01); *A61M 2205/50* (2013.01); *A61M 2205/581* (2013.01); *A61M 2205/582* (2013.01); *A61M 2205/583* (2013.01);
(Continued)

(58) Field of Classification Search
CPC ............ A61M 5/14276; A61M 5/1723; A61M 5/14244; A61M 5/172; G16H 20/17; A61N 1/36139
See application file for complete search history.

(56) References Cited

U.S. PATENT DOCUMENTS

| 4,502,488 A | 3/1985 | Degironimo et al. |
| 4,730,623 A | 3/1988 | Lee |

(Continued)

FOREIGN PATENT DOCUMENTS

| EP | 0226220 A2 | 6/1987 |
| EP | 1 345 640 B1 | 9/2003 |
| WO | WO2018119179 A1 | 6/2018 |

OTHER PUBLICATIONS

International Search Report and Written Opinion for PCT/US2020/043252, dated Oct. 5, 2020, 12 pages.

(Continued)

*Primary Examiner* — Manuel A Mendez
(74) *Attorney, Agent, or Firm* — Patterson Thuente Pedersen, P.A.

(57) ABSTRACT

An intrathecal drug delivery system configured to monitor one or more physiological conditions of the patient to look for opportunities to time medicament delivery to coincide with patient activity inferring heightened cerebrospinal fluid oscillations, thereby improving dispersion of the medicament within the intrathecal space of the patient. The intrathecal drug delivery system includes an implantable medical pump, one or more physiological sensors, and an external programmer configured to program the implantable medical pump with a treatment protocol specifying at least one period of time during which a specified quantity of medicament is to be administered during which the implantable medical pump utilizes data from the one or more physiological sensors to time delivery of the medicament.

15 Claims, 5 Drawing Sheets

(52) U.S. Cl.
CPC . *A61M 2210/1003* (2013.01); *A61M 2230/06* (2013.01); *A61M 2230/205* (2013.01); *A61M 2230/40* (2013.01); *A61M 2230/62* (2013.01); *A61M 2230/63* (2013.01)

(56) References Cited

U.S. PATENT DOCUMENTS

| | | | |
|---|---|---|---|
| 4,731,051 A * | 3/1988 | Fischell | A61M 5/14276 604/67 |
| 4,834,709 A | 5/1989 | Banning et al. | |
| 5,807,324 A | 9/1998 | Griffin, III | |
| 6,579,280 B1 | 6/2003 | Kovach et al. | |
| 6,807,965 B1 | 10/2004 | Hickle | |
| 7,072,802 B2 | 7/2006 | Hartlaub | |
| 7,192,414 B2 | 3/2007 | Stultz | |
| 7,438,701 B2 | 10/2008 | Theeuwes et al. | |
| 7,593,770 B2 | 9/2009 | Lerner | |
| 7,651,518 B2 | 1/2010 | Dobak, III et al. | |
| 7,806,886 B2 | 10/2010 | Kanderian et al. | |
| 8,486,023 B2 | 7/2013 | Pyles | |
| 9,122,785 B2 | 9/2015 | Alme et al. | |
| 9,655,528 B2 | 5/2017 | Zhu | |
| 9,682,193 B2 | 6/2017 | Anand et al. | |
| 9,770,180 B2 * | 9/2017 | Radojicic | A61M 25/00 |
| 2006/0178617 A1 | 8/2006 | Adams et al. | |
| 2007/0137296 A1 | 6/2007 | Krivitski et al. | |
| 2008/0146990 A1 | 6/2008 | Jenson et al. | |
| 2010/0125246 A1 | 5/2010 | Kalpin | |
| 2012/0197322 A1 * | 8/2012 | Skelton | A61N 1/3787 607/2 |
| 2013/0296823 A1 | 11/2013 | Melker et al. | |
| 2014/0228765 A1 | 8/2014 | Burke et al. | |
| 2019/0160254 A1 | 5/2019 | Anand et al. | |

OTHER PUBLICATIONS

International Search Report and Written Opinion for PCTU.S. Pat. No. 2020043249, dated Nov. 16, 2020, 10 pages.
Extended European Search Report for European Application No. 19179065.8, dated Aug. 9, 2019.
Sakka et al., "Anatomy and physiology of cerebrospinal fluid," European Annals of Otorhinolaryngology, Head and Neck diseases (2011) 128, 309-316. Available online Nov. 18, 2011.

* cited by examiner

OPTIMIZED INTRATHECAL DRUG DELIVERY

RELATED APPLICATION INFORMATION

This application claims the benefit of U.S. Provisional Application No. 62/687,889, filed Jun. 21, 2018, the contents of which are fully incorporated herein by reference.

TECHNICAL FIELD

The present disclosure relates generally to implantable medical devices, and more particularly to a system and method configured to utilize patient activity to optimize intrathecal medicament delivery.

BACKGROUND

A variety of medical devices are used for chronic, i.e., long-term, delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, pumps or other fluid delivery devices can be used for chronic delivery of therapeutic medicaments, such as drugs or other agents. Typically, such devices provide therapy continuously or periodically according to programmed parameters. The programmed parameters can specify the therapeutic regimen (e.g., the rate, quantity, and timing of medicament delivery to a patient), as well as other functions of the medical device.

Implantable medical infusion pumps have important advantages over other forms of medicament administration. For example, oral administration is often not workable because the systematic dose of the substance needed to achieve the therapeutic dose at the target site may be too large for the patient to tolerate without very adverse side effects. Also, some substances simply cannot be absorbed in the gut adequately for a therapeutic dose to reach the target site. Moreover, substances that are not lipid soluble may not cross the blood brain barrier adequately if needed in the brain. In addition, infusion of substances from outside the body requires a transcutaneous catheter, which results in other risks such as infection or catheter dislodgment. Further, implantable medical pumps avoid the problem of patient noncompliance, namely the patient failing to take the prescribed drug or therapy has instructed.

Implantable medical infusion pumps are typically implanted at a location within the body of a patient (typically a subcutaneous region in the lower abdomen), and are configured to deliver a fluid medicament through a catheter. The catheter is generally configured as a flexible tube with a lumen running the length of the catheter to a selected delivery site in the body, such as the spinal canal or subarachnoid space. Such implantable medical pumps typically include an expandable fluid reservoir, which is accessible for refill etc. through an access port. Medicament flows from the reservoir via the lumen in the catheter according to programmed parameters.

In some cases, the implantable medical pump can be configured to receive the programmed parameters and other updates from an external programming device, sometimes referred to as a controller or programmer, which can communicate with the implantable medical pump through well-known techniques such as wireless telemetry. The external programmer can be used by a clinician or patient to change the therapeutic regimen, for example by defining a treatment protocol. Typically, a clinician or patient interfaces with the external programmer to set various parameters associated with the implantable medical pump, and then transmits or downloads those parameters to the implantable medical pump.

Although various attempts have been made to adjust the programmed parameters to increase the efficacy of medicament delivery, typically through patient feedback via direct or indirect monitoring of the patient's condition, it is desirous to further improve the efficiency of intrathecal drug delivery. Applicants of the present disclosure have developed a system and method to address this concern.

SUMMARY OF THE DISCLOSURE

Embodiments of the present disclosure provide a system and method of using increased patient activity to optimize intrathecal medicament delivery. Intrathecal drug dispersion in the cerebrospinal fluid is largely driven by the periodic oscillations of the cerebrospinal fluid itself. The periodic oscillations of the cerebrospinal fluid are correlated with cardiac contractions and respiration, such that a generally increased respiratory or heart rate typically corresponds with an increase in the frequency (and to a lesser extent magnitude or amplitude) of the cerebrospinal fluid oscillations. Accordingly, delivery of a bolus of medicament during a period of relatively higher respiration and heart rate can be more effective than delivery of the same bolus during a period of relative rest (e.g., sleep). Embodiments of the present disclosure employ a system and method wherein a bolus is programmed for delivery within a predefined window of time, instead of at a precise moment. The predefined window of time (e.g., one hour) enables the system to look for opportunities to time the bolus delivery with increases in cerebrospinal fluid oscillations, as measured by increases in patient heart rate and respiration.

One embodiment of the present disclosure provides intrathecal drug delivery system configured to monitor one or more physiological conditions of the patient to look for opportunities to time medicament delivery to coincide with a desired posture of the patient or patient activity inferring heightened cerebrospinal fluid oscillations, thereby improving dispersion of the medicament within the intrathecal space of the patient. The intrathecal drug delivery system can include an implantable medical pump, one or more physiological sensors, and an external programmer. The implantable medical pump can be configured to deliver medicament within the intrathecal space of a patient. The one or more physiological sensors can be configured to monitor one or more physiological conditions of the patient. The external programmer can be configured with a treatment protocol specifying at least one period of time during which a specified quantity of medicament is to be administered. During the at least one period of time, the implantable medical pump can utilize data from the one or more physiological sensors to time delivery of the medicament.

In one embodiment, at least one of the one or more physiological sensors is a heart rate monitor, pulse oximeter, respiratory sensor, perspiration sensor, posture orientation sensor, motion sensor, or accelerometer. In one embodiment, at least one of the one or more physiological sensors is incorporated into the implantable medical pump. In one embodiment, at least one of the one or more physiological sensors is worn by the patient. In one embodiment, at least one of the one or more physiological sensors wirelessly communicates with the implantable medical pump. In one embodiment, at least one of the one or more physiological sensors continuously monitors a physiological condition of the patient. In one embodiment, the system further comprises a server configured to receive and store data from at least one of the one or more physiological sensors. In one embodiment, data from at least one of the one or more physiological sensors is used to establish a patient specific active state threshold. In one embodiment the patient specific active state threshold is utilized as a trigger for the delivery of medicament. In one embodiment the at least one period of time is defined to begin in a specified time of day and extend for a defined duration.

Another embodiment of the present disclosure provides a method of intrathecal drug delivery comprising: programming an implantable medical pump with a treatment protocol specifying at least one period of time during which a specified quantity of medicament is to be delivered into the intrathecal space of a patient; monitoring one or more physiological conditions of the patient with one or more physiological sensors to determine a posture of the patient or patient activity inferring heightened cerebrospinal fluid oscillations; and timing the delivery of the medicament to coincide with a desired posture of the patient or patient activity inferring heightened cerebrospinal fluid oscillations, thereby improving dispersion of the medicament within the intrathecal space of the patient.

In one embodiment, at least one or more of the monitored physiological conditions is a posture, heart rate or respiratory rate of the patient. In one embodiment, at least one of the one or more physiological sensors continuously monitors a physiological condition of the patient. In one embodiment, the method further comprises receiving and storing data from at least one of the one or more physiological sensors on at least one of a server or external programmer. In one embodiment, the method further comprises utilizing the stored data from at least one of the one or more physiological sensors to establish a patient specific active state threshold. In one embodiment, patient specific active state threshold is utilized as a trigger for delivery of medicament.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
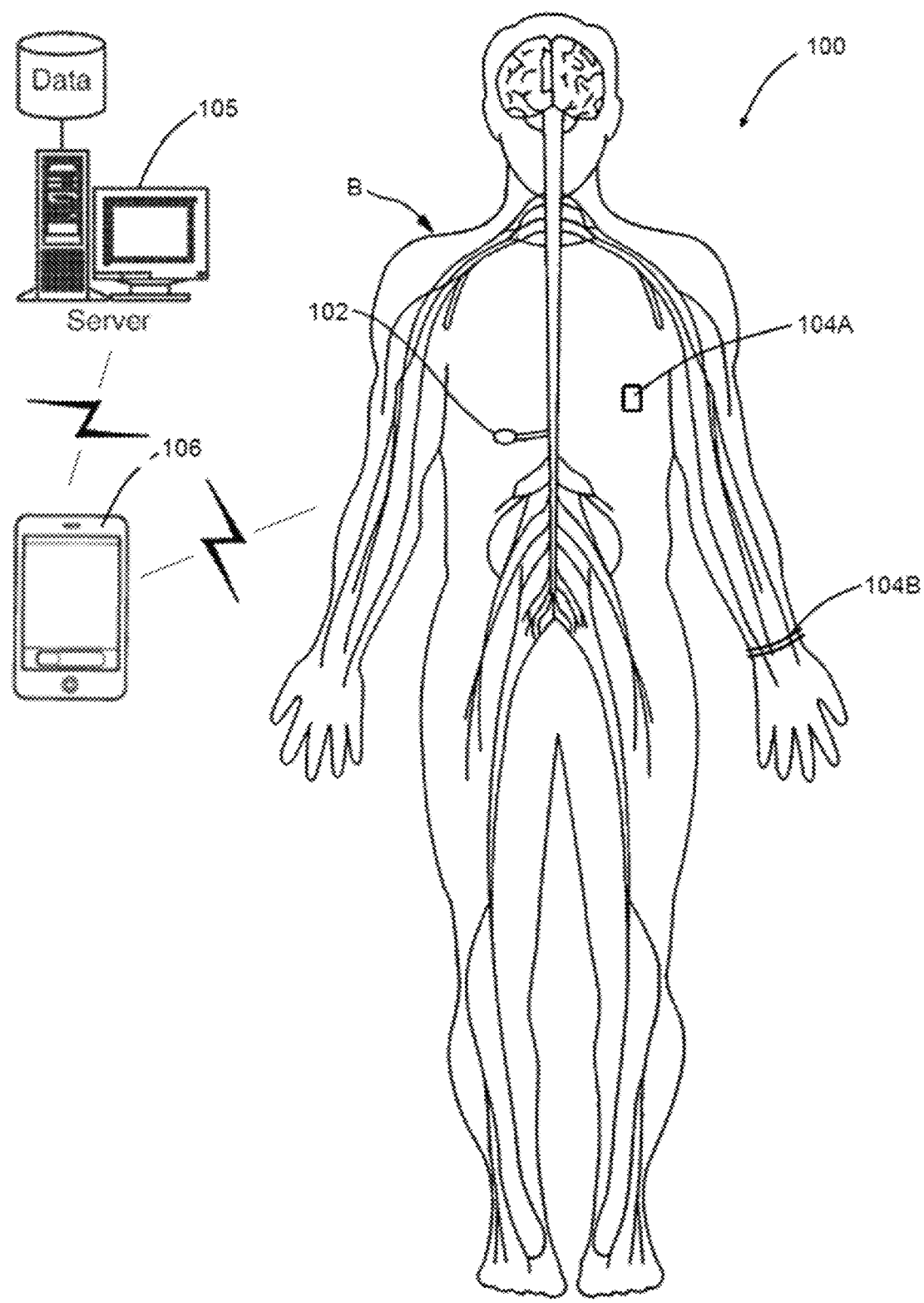
FIG. 1 is a schematic view depicting an intrathecal drug delivery system in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a schematic view of an intrathecal drug delivery system 100 is depicted in accordance with an embodiment of the disclosure. The intrathecal drug delivery system 100 can include an implantable medical pump 102, one or more physiological sensors 104 (such as sensors 104A and 104B), and optional server 105, and an optional external programmer 106.

Figure 2:
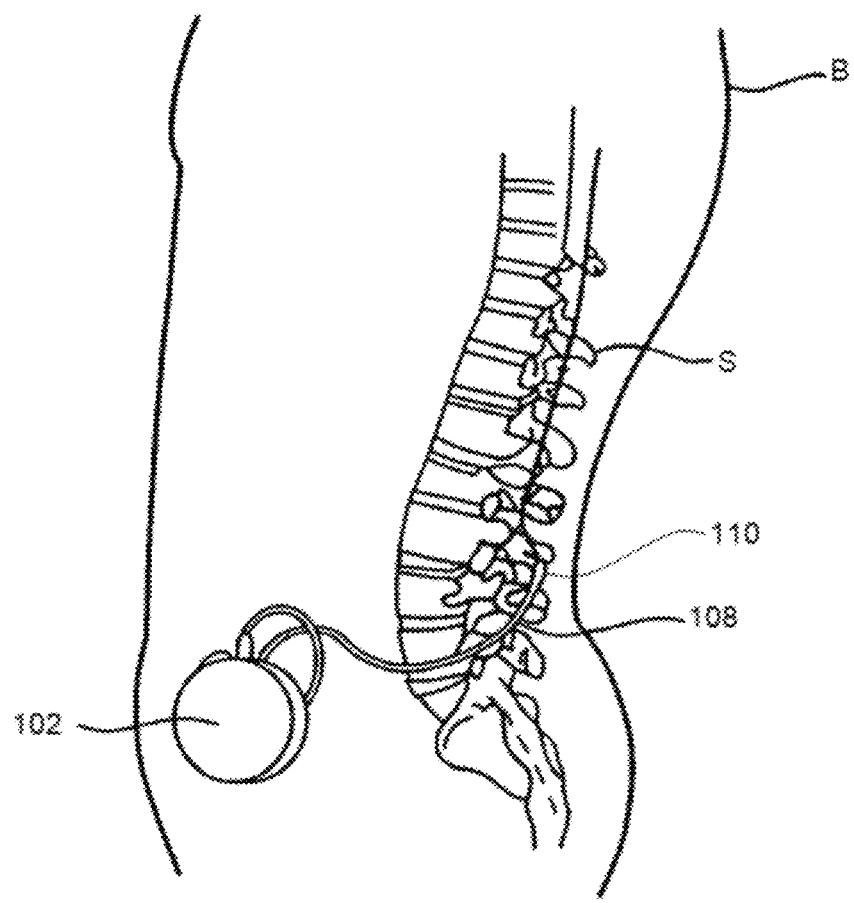
FIG. 2 depicts an implantable medical pump in accordance with an embodiment of the disclosure implanted within a body of a patient.

Referring to FIG. 2, an implantable medical pump 102 in accordance with an embodiment of the disclosure is depicted as being implanted within the body B of a patient. The implantable medical pump 102 can be in fluid communication with a catheter 108 having a distal tip 110 positioned within the subarachnoid space of the patient's spine S, thereby enabling intrathecal delivery of medicament through a lumen of the catheter 108.

Figure 3:
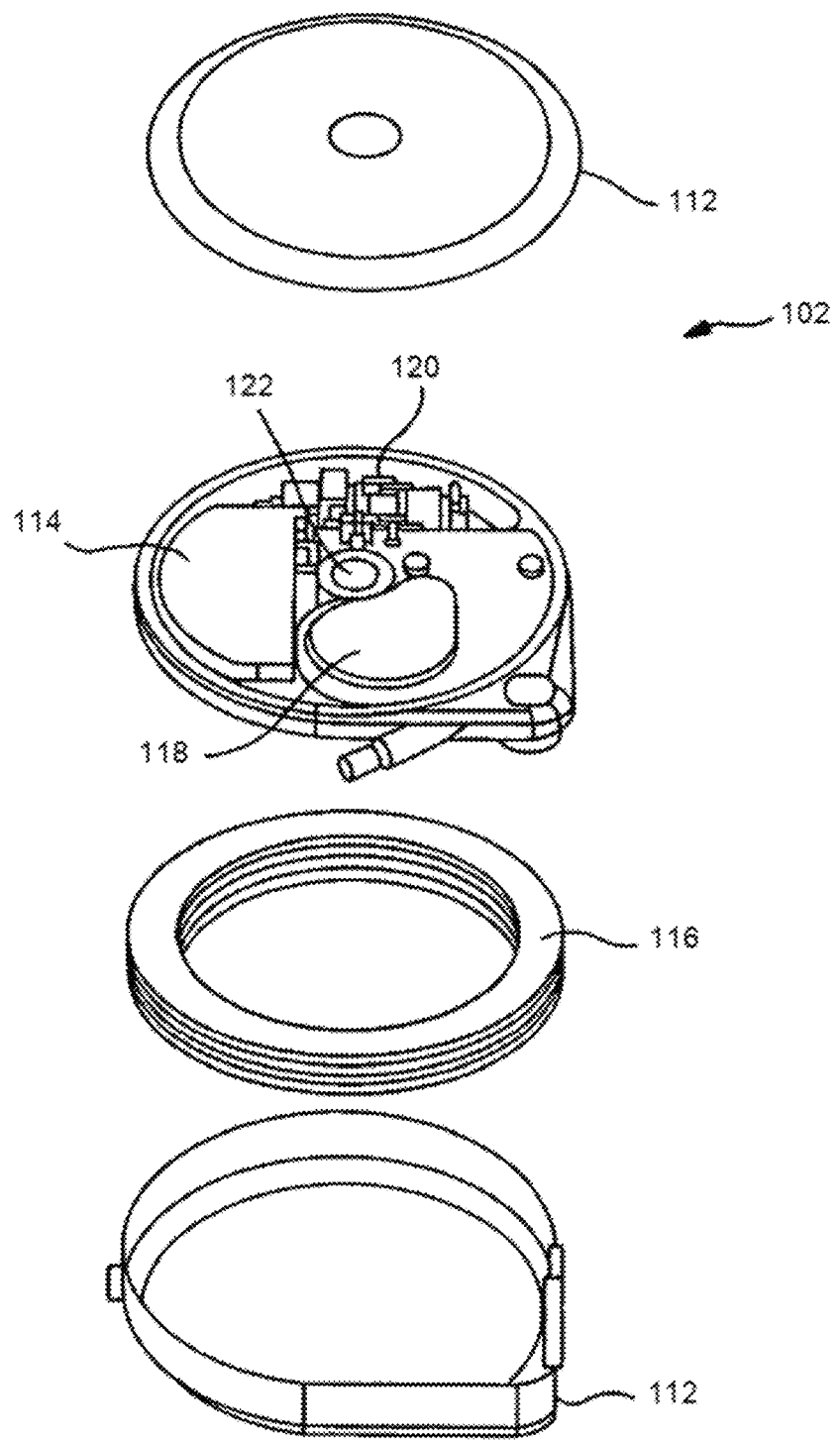
FIG. 3 is an exploded perspective view depicting an implantable medical pump in accordance with an embodiment of the disclosure.
Figure 4:
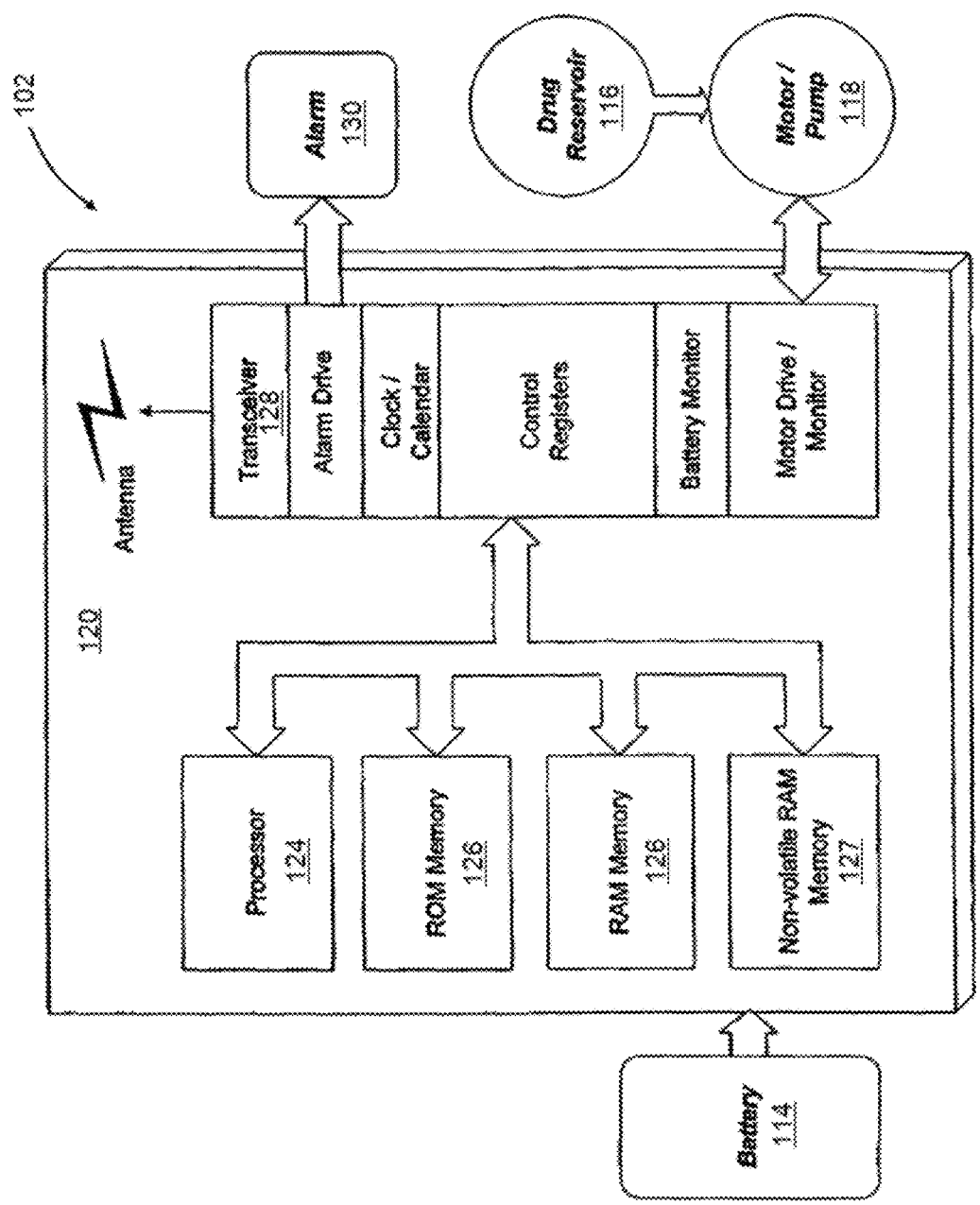
FIG. 4 is a block diagram depicting an implantable medical pump in accordance with an embodiment of the disclosure.

Referring to FIG. 3, an exploded perspective view of an implantable medical pump 102 is depicted in accordance with an embodiment of the disclosure. Referring to FIG. 4, a block diagram of an implantable medical pump 102 is depicted in accordance with an embodiment of the disclosure. The implantable medical pump 102 can generally include a housing 112, power source 114, medicament reservoir 116, medicament pump 118, and electronics 120. The housing 112 can be constructed of a material that is biocompatible and hermetically sealed, such as titanium, tantalum, stainless steel, plastic, ceramic, or the like. The power source 114 can be a battery, such as a lithium-ion battery. The power source 114 can be carried in the housing 112, and can be selected to operate the medicament pump 118 and electronics 120.

The medicament reservoir 116 can be carried by the housing 112 and can be configured to contain medicament. In one embodiment, medicament within the medicament reservoir 116 can be accessed via an access port 122. Accordingly, the access port 122 can be utilized to refill, empty, or exchange the fluid within the medicament reservoir 116.

The medicament pump 118 can be carried by the housing 112. The medicament pump 118 can be in fluid communication with the medicament reservoir 116 and can be in electrical communication with the electronics 120. The medicament pump is a pump that is sufficient for infusing medicament to the patient, such as a piston pump, a peristaltic pump, a pump powered by a stepper motor, a pump powered by an AC motor, a pump powered by a DC motor, an electrostatic diaphragm, a piezoelectric motor, a solenoid, a shape memory alloy, or the like.

The electronics 120 are carried in the housing 112, and can be in electrical communication with the power source 114 and medicament pump 118. In one embodiment, the electronics 120 can include a processor 124, memory 126 and 127, and transceiver circuitry 128. In one embodiment, the processor 124 can be in Application-Specific Integrated Circuit (ASIC) state machine, gate array, controller, or the like. The electronics 120 can be generally configured to control infusion of medicament according to programmed parameters or a specified treatment protocol. The programmed parameters or specified treatment protocol can be stored in the memory 126. The transceiver circuitry 128 can be configured to receive information from and transmit information to the one or more physiological sensors 104 and external programmer 106. In one embodiment, the electronics 120 can be further be configured to operate a number of other features, such a patient alarm 130.

The implantable medical pump 102 is configured to receive programmed parameters and other updates from the external programmer 106, which can communicate with the implantable medical pump 102 through well-known techniques such as wireless telemetry. In some embodiments, the external programmer 106 can be configured for exclusive communication with one or more implantable medical pumps 102 and physiological sensors 104. In other embodiments, the external programmer 106 can be any computing platform, such as a mobile phone or tablet. In some embodiments, the external programmer 106 can further be in communication with a cloud-based server 105. The server 105 can be configured to receive, store and transmit information, such as program parameters, treatment protocols, drug libraries, and patient information, as well as to receive and store data recorded by the implantable medical pump 102 or physiological sensors 104.

The distal tip 110 of the catheter 108 can extend into the subarachnoid space of a patient's spine, thereby enabling delivery of medicament into the cerebrospinal fluid of the patient. The cerebrospinal fluid resides within the brain ventricles and the cranial and spinal subarachnoid spaces. Cerebrospinal fluid circulation is a dynamic phenomenon closely correlated with the patient's arterial pulse wave; although other factors, such as respiratory waves, the patient's posture, jugular venous pressure, and physical effort may also affect cerebrospinal fluid flow dynamics and pressure. The cerebrospinal fluid volume is estimated to be about 150 mL in adults, with approximately 125 mL located in the cranial and spinal subarachnoid spaces and the remaining 25 mL located in the brain ventricles. Through normal pulsatile flow, the cerebrospinal fluid is renewed about four times every 24 hours.

The physiological sensors 104 can be any sensor configured to monitor one or more physiological conditions affecting cerebrospinal fluid circulation. Examples of physiological sensors 104 include a heart rate monitor, pulse oximeter, respiratory sensor, perspiration sensor, posture orientation sensor, motion sensor, accelerometer, or the like. In some embodiments, an increase in patient activity (as measured by an increase in heart rate, respiratory rate, etc.) can infer an increase in frequency of cerebrospinal fluid oscillations, which in turn can improve mixing of the medicament with the cerebrospinal fluid. In some embodiments, a particular posture of a patient may be desirable for improved mixing of the medicament. For example, some medicaments are not neutrally buoyant, and therefore are affected by gravity; timing delivery of these types of medicament to coincide with a generally horizontal or generally vertical posture can improve dispersion.

In one embodiment, a physiological sensors can incorporated into the implantable medical pump. In one embodiment, a physiological sensor 104 can be worn by the patient (e.g., a smart watch, wristband tracker, sensors embedded in clothing, etc.), carried by the patient (e.g., a smart phone, etc.), or positioned in proximity to the patient (e.g., a stationary monitor, etc.). In one embodiment, the external programmer 106 can include one or more physiological sensors 104. Data from one or more physiological sensors 104 can be utilized to determine an increased rate of activity by the patient, which can infer an increase in the frequency of cerebrospinal fluid oscillations. In some embodiments, conditions sensed by the one or more sensors 104 can be communicated to the external programmer 106 for processing. In other embodiments, the one or more sensors 104 can communicate directly with the implantable medical pump 102.

Figure 5:
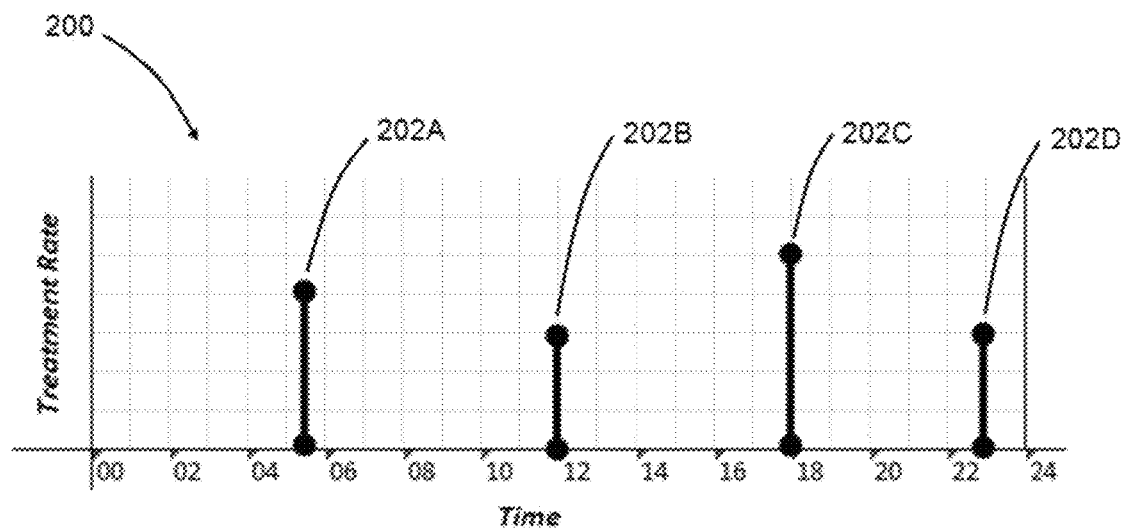
FIG. 5 depicts a manner of specifying a treatment protocol of the prior art.

Referring to FIG. 5, a manner of specifying a treatment protocol 200 for programming an implantable medical pump is depicted according to the prior art. The vertical axis represents the medicament treatment rate (e.g., the bolus quantity to be infused), and the horizontal axis represents elapsed time. As depicted, the treatment protocol 200 calls for the delivery of four boluses 202A-D over the course of a 24 hour period. When the treatment protocol 200 is programmed into an implantable medical pump, the pump will carry out instructions of the protocol 200. In particular, the implantable medical pump 102 will deliver 200 µL of medicament to the patient at 5:30 AM (the first bolus 202A); 150 µL of medicament at 12 PM (the second bolus 202B); 250 µL of medicament at 6 PM (the third bolus 202C); and 150 µL of medicament at 11 PM (the fourth bolus 202D). It should be understood that the figures represent each bolus delivery as a singular moment in time, in reality a bolus may take several minutes to deliver based on the infusion rates that are possible for a particular pump design. Accordingly, the bolus deliveries begin at the scheduled time and continue until the prescribed quantity of medicament has been administered, regardless of the condition or state of the patient. In some cases, a condition or state of the patient can be monitored after delivery in order to ascertain the efficiency of the bolus delivery.

Figure 6:
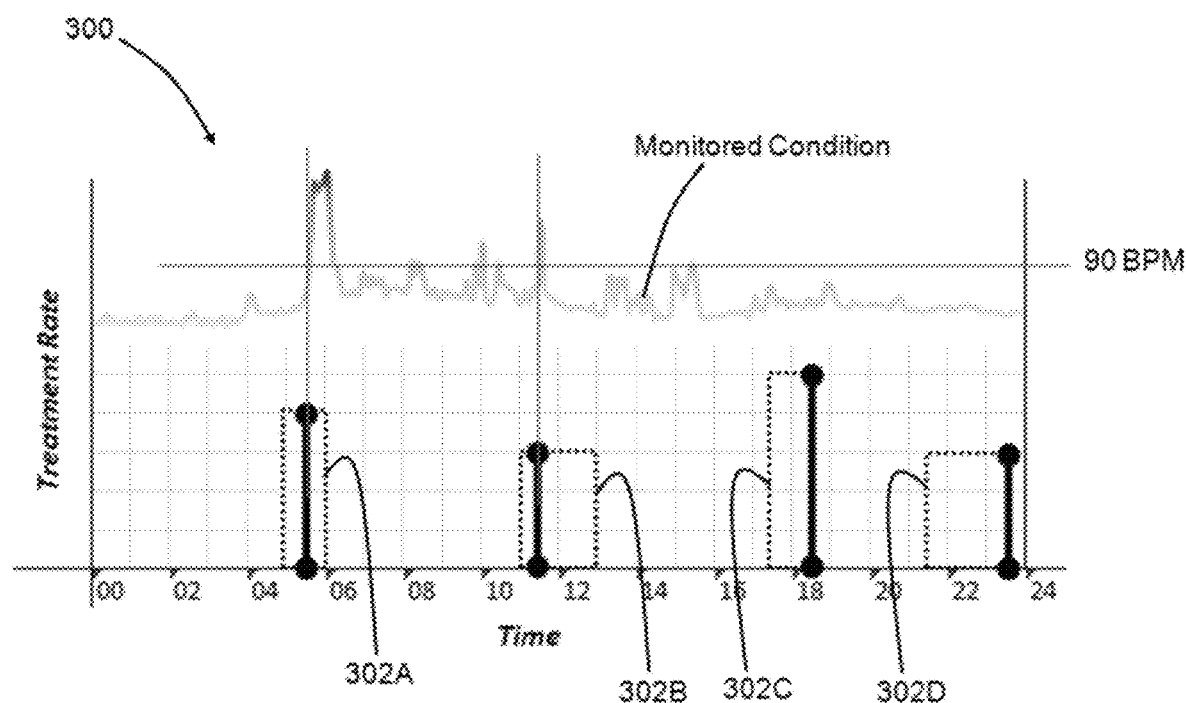
FIG. 6 depicts a manner of specifying a treatment protocol in accordance with an embodiment of the disclosure.

Referring to FIG. 6, a manner of specifying a treatment protocol 300 programming an implantable medical pump 102 is depicted in accordance with an embodiment of the disclosure. The vertical axis represents the medical treatment rate (e.g., the bolus quantity to be infused), and a horizontal axis represents the elapsed time. However, unlike the prior art, the treatment protocol 300 defines one or more periods or windows of time 302A-D during which a specified quantity of medicament is to be administered. For example, as depicted, the treatment protocol 300 calls for a delivery of 200 µL of medicament between 5-6 AM (the first window 302A); delivery of 150 µL of medicament between 11 AM-1 PM (the second window 302B); delivery of 250 µL of medicament between 5:30-6:30 PM (the third window 302C); and delivery of 150 µL of medicament between 9:30-11:30 PM (the fourth window 302D). When the treatment protocol 300 is programmed into the implantable medical pump 102, via the external programmer 106, the intrathecal drug delivery system 100 monitors physiological conditions of the patient to look for opportunities to time the delivery of medicament with a desirable posture of the patient or perceived increases in cerebrospinal fluid oscillations. Thus, unlike the prior art, bolus deliveries do not begin at a specified time, but rather are triggered by physiological conditions of the patient. Although periods of one and two hours are utilized for periods of time 302A-D in this example, other durations of time in which a specified quantity of medicament is to be administered are also contemplated.

In some embodiments, the physiological sensor 104 can be configured to monitor one or more conditions of the patient continuously. In other embodiments, the physiological sensor 104 is limited to sensing patient conditions during the one or more periods of time 302A-D in which a specified quantity of medicament is to be administered. Data collected by one or more physiological sensors 104 can be utilized to establish patient specific baselines or thresholds; for example, a resting state baseline (e.g., less than 70 bpm) and an active state threshold (e.g., greater than 90 bpm). In one embodiment, the resting state baseline or active state threshold can be utilized to trigger to initiate administration of medicament. In one embodiment, one or more baselines or thresholds can be utilized to trigger the administration of medicament; for example, different baselines or thresholds can be established during different times of the day. In one embodiment, administration of medicament can be triggered based on a rate of change of the activity (e.g., using a derivative of a sensed or measured physiological condition of the patient). In one embodiment, the one or more established baselines or thresholds can serve as initial defaults, and can be manually adjusted by a clinician or patient via the external programmer 106. For example, in one embodiment, a patient can input activity schedule information (e.g., workout times, etc.) and adjust the baseline or thresholds accordingly.

In the example embodiment depicted in FIG. 6, a physiological sensor 104 continuously monitors the heart rate of the patient. During the first window 302A, the intrathecal drug delivery system 100 monitors the heart rate of the patient to look for an opportunity to time the administration of medicament with a perceived increase in cerebrospinal fluid oscillations. In particular, the intrathecal drug delivery system 100 begins looking for an opportunity at 5 AM. At approximately 5:35 AM, the sensed heart rate of the patient exceeds the active state threshold of 90 bpm, thereby triggering the delivery of medicament. The delivery of medicament continues until 200 µL has been dispensed.

During the second window 302B, the intrathecal drug delivery system 100 again monitors the heart rate of the patient, this time beginning at 11 AM. At approximately 11:23 AM, the sensed heart rate of the patient exceeds 90 bpm and the administration of 150 µL of medicament is commenced.

During the third and fourth windows 302C, 302D, the intrathecal drug delivery system monitors the heartrate that the patient, but the patient's heart rate never exceeds the active state threshold. At the end of the window (6:30 PM and 11:30 PM respectively), the administration of medicament in the prescribed amount is commenced. Thus, if no opportunity to time the delivery of medicament with an increase in patient activity is perceived, the prescribed bolus is delivered at the end of the window 302.

Accordingly, unlike the prior art in which one or more conditions of a patient can be monitored after delivery of a bolus to ascertain the efficacy of the bolus delivery, the intrathecal drug delivery system 100 of the present disclosure utilizes data sensed by one or more physiological sensors to look for opportunities to time (e.g., initiate and carry out) delivery, in order to optimize intrathecal drug delivery. In other words, whereas the prior art utilizes monitored patient conditions to evaluate past events (i.e., the data is used in a backward looking manner), embodiments of the present disclosure utilized monitored patient conditions to guide future events (i.e., the data is used in a forward looking manner).

In one embodiment, physiological data collected over a longer period of time (e.g., several days or weeks) can be utilized to suggest improvements to a programmed treatment protocol 300. For example, based on the collected data, the intrathecal drug delivery system 100 can identify natural patterns of patient posture or increased patient activity, which can present opportunities to time bolus administration for the further optimization of medicament delivery. In one embodiment, the intrathecal drug delivery system 100 can utilize predictive algorithms for determining whether the patient's activity level is more likely to go up or down during the window 302, to initiate or delay the delivery of medicament accordingly. In one embodiment, the intrathecal drug delivery system 100 can suggest moving a window 302 earlier or later in the day to coincide with an established pattern of increased patient activity. In another embodiment, the intrathecal drug delivery system 100 can suggest increasing the duration of a window 302, such that the window 302 coincides with an increase in patient activity that generally occurs during a particular time of the day, but occurs with some variation (e.g., a period of increased activity that normally occurs around 11 AM+/−1 hour). In one embodiment, the intrathecal drug delivery system 100 can further adjust the delivery (e.g., rate or amount) based on the patient's posture or measured activity level at the time that the medicament delivery is triggered.

In one embodiment, the intrathecal drug delivery system 100 can provide a notification to the patient regarding the timing of the window 302 for delivery of medicament. For example, in one embodiment, the patient can be notified that the window 302 is open or is about to close. In one embodiment, the intrathecal drug delivery system 100 can further suggest that the patient modify their posture or increase their activity to a desirable level. Such notifications can be sent to the external programmer 106, for example in a visual form, or to one or more of the physiological sensors 104 or external programmer 106 in the form of a vibration or audio signal.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An intrathecal drug delivery system configured to monitor one or more physiological conditions of a patient to look for opportunities to time medicament delivery to coincide with patient activity inferring heightened cerebrospinal fluid oscillations, thereby improving dispersion of the medicament within an intrathecal space of the patient, the intrathecal drug delivery system comprising:
    an implantable medical pump configured to deliver medicament within the intrathecal space of a patient;
    one or more physiological sensors configured to monitor at least one of a heart rate, respiratory rate, oxygen saturation, or perspiration rate of the patient; and
    an external programmer configured to program the implantable medical pump with a treatment protocol specifying at least one period of time during which a specified quantity of medicament is to be administered,
    wherein during the at least one period of time, the implantable medical pump is configured to administer the specified quantity of medicament upon at least one of the monitored heart rate, respiratory rate, oxygen saturation, or perspiration rate meeting or exceeding a patient specific active state threshold.

2. The intrathecal drug delivery system of claim 1, wherein at least one of the one or more physiological sensors further comprise an orientation sensor, motion sensor, or accelerometer.

3. The intrathecal drug delivery system of claim 1, wherein at least one of the one or more physiological sensors is at least one of incorporated into the implantable medical pump or worn by the patient.

4. The intrathecal drug delivery system of claim 1, wherein at least one of the one or more physiological sensors wirelessly communicates with the implantable medical pump.

5. The intrathecal drug delivery system of claim 1, wherein at least one of the one or more physiological sensors continuously monitors a physiological condition of the patient.

6. The intrathecal drug delivery system of claim 1, wherein data from at least one of the one or more physiological sensors is used to establish the patient specific active state threshold.

7. The intrathecal drug delivery system of claim 6, wherein the patient specific active state threshold is utilized as a trigger for the delivery of medicament.

8. The intrathecal drug delivery system of claim 1, wherein the at least one period of time is defined to begin at a specified time of day and extend for a defined duration.

9. The intrathecal drug delivery system of claim 1, wherein the intrathecal drug delivery system is further configured to provide a notification to suggest at least one of modifying patient posture to the desired posture or increasing patient activity.

10. A method of timing intrathecal drug delivery to correspond with heightened cerebrospinal fluid oscillations, the method comprising:
    programming an implantable medical pump with a treatment protocol specifying at least one period of time during which a specified quantity of medicament is to be delivered into the intrathecal space of patient;
    monitoring one or more physiological conditions of the patient with one or more physiological sensors to determine at least one of a heart rate, respiratory rate, oxygen saturation, or perspiration rate; and
    timing the delivery of the medicament to coincide with at least one of the monitored heart rate, respiratory rate, oxygen saturation, or perspiration rate meeting or exceeding a patient specific active state threshold, thereby improving dispersion of the medicament within the intrathecal space of the patient.

11. The method of claim 10, further comprising monitoring a posture of the patient.

12. The method of claim 10, wherein at least one of the one or more physiological sensors continuously monitors a physiological condition of the patient.

13. The method of claim 12, further comprising receiving and storing data from at least one of the one or more physiological sensors on at least one of a server or external programmer.

14. The method of claim 13, further comprising utilizing the stored data from at least one of the one or more physiological sensors to establish the patient specific active state threshold.

15. The method of claim 14, wherein the patient specific active state threshold is utilized as a trigger for the delivery of medicament.

* * * * *